United States Patent
Vellut et al.

(10) Patent No.: US 6,364,523 B1
(45) Date of Patent: Apr. 2, 2002

(54) EBULLIOMETRIC DEVICE FOR MEASURING WITH HIGH PRECISION A PHYSICAL PARAMETER OF LIQUID SUBSTANCES

(75) Inventors: David Vellut, Craponne; Jacques Jose, Villette de Vienne; Emmanuel Behar, Jouy le Moutier, all of (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/500,240

(22) Filed: Feb. 8, 2000

(30) Foreign Application Priority Data

Feb. 9, 1999 (FR) .............................................. 99 01541

(51) Int. Cl.[7] ......................... G01N 25/00; G01N 25/02
(52) U.S. Cl. ............................................ 374/45; 374/27
(58) Field of Search ............................... 374/16, 27, 45

(56) References Cited

U.S. PATENT DOCUMENTS

| | | | |
|---|---|---|---|
| 2,900,816 A | | 8/1959 | Anderson |
| 3,698,235 A | * | 10/1972 | Mikhailov et al. ............. 374/27 |
| 3,794,566 A | * | 2/1974 | Raal .............................. 374/27 |
| 4,250,739 A | * | 2/1981 | Audeh et al. .................. 374/27 |
| 4,408,902 A | * | 10/1983 | Peuker ......................... 374/27 |
| 4,484,822 A | * | 11/1984 | Hancock ....................... 374/16 |
| 4,523,860 A | * | 6/1985 | Chin et al. .................... 374/27 |
| 4,528,635 A | * | 7/1985 | Juodikis et al. ................ 374/27 |
| 4,549,816 A | * | 10/1985 | Fujioka ........................ 374/27 |

FOREIGN PATENT DOCUMENTS

| | | |
|---|---|---|
| AU | 4273489 | 4/1990 |
| CH | 415118 | 12/1966 |
| FR | 2087616 | 12/1971 |
| FR | 2410818 | 6/1979 |

* cited by examiner

Primary Examiner—Diego Gutierrez
Assistant Examiner—Yaritza Guadalupe
(74) Attorney, Agent, or Firm—Antonelli, Terry, Stout & Kraus, LLP

(57) ABSTRACT

An ebulliometric device measures with high precision a physical parameter of a liquid substance. It includes an ebulliometer having an elongate vessel into which a liquid substance is fed, a sensor for measuring the boiling-point temperature arranged in the upper part of the vessel, a pump allowing to spray substance in the form of liquid and vapor in the upper part of the vessel, and an assembly external to the vessel for condensing the vapor allowing to recycle the condensed vapor to the base of the vessel and at least one thermostat-controlled enclosure. The device also includes a first finger tube extending in the elongate vessel from an upper part of the same for protecting the sensor, an element in close contact with the first finger tube for increasing a time of contact of liquid and vapor with the finger tube, a second tube delimiting a containment space around the first tube and the element, this space communicating with the pump through a duct, and gas injecting means at an lower part of the elongate vessel for controlling the boiling temperature.

19 Claims, 2 Drawing Sheets

EBULLIOMETRIC DEVICE FOR MEASURING WITH HIGH PRECISION A PHYSICAL PARAMETER OF LIQUID SUBSTANCES

FIELD OF THE INVENTION

The present invention relates to an ebulliometric device for measuring with high precision a physical parameter of liquid substances, such as the temperature thereof, and to its application for determining the molar mass of substances.

The device is notably suited for determining molar masses by means of fine measurement of the boiling temperature difference between the boiling-point temperature of a pure solvent and that of a solution where a solute is dissolved in the same solvent.

The device according to the invention is suited for various applications in many fields, and notably for petroleum cut analysis in order to determine for example the proportion of each constituent distributed according to its chemical family and to the number of carbon atoms contained therein.

BACKGROUND OF THE INVENTION

The principle of determination of the molar mass of a substance or of a mixture of substances by means of an ebulliometer is known in the art. It consists in measuring with precision, at a set pressure, the difference between the boiling-point temperature of a pure solvent and that of the same solvent in which the substance studied is dissolved, and in deducing its molar mass therefrom An ebulliometer generally comprises an elongate vessel where the mixture to be measured is boiled at a controlled pressure, a temperature detector placed above the liquid phase, pumping means allowing to spray, in the vicinity of the temperature detector, a liquid-vapour mixture at equilibrium, taken at the base of the vessel, and recycling means including a condenser, for recycling the vapour phase to this base of the vessel.

Various ebulliometers are described for example by Olson J. D., "Measurement of Vapor-Liquid Equilibria by Ebulliometer" in Fluid Phase Equilibria, 52 (1989) 209–218; Elsevier Science Publishers, or in patents FR-2,636,430 or AU-A-42,734/89.

The problem in this type of measurement is to obtain a stable temperature so as to reduce the possible temperature fluctuation margin, which requires close ebullition control so as to ensure that the temperature measured is the temperature at equilibrium of the mixture of liquid and gas phases.

SUMMARY OF THE INVENTION

The device according to the invention allows to measure with high precision a physical parameter of liquid substances (their boiling-point temperature or a characteristic depending thereon, linked with the composition thereof), comprising at least one ebulliometer including an elongate vessel into which a liquid substance is fed, means for boiling the liquid, a means for measuring the temperature, placed in the upper part of the vessel, a pumping means allowing to spray substance in the form of liquid and vapour towards the upper part of the vessel, means external to the vessel for condensing the vapour and allowing to recycle it to the base of the vessel.

It is characterized in that it comprises a first tube into which is lowered the means for measuring the temperature in the upper part of the enclosure, a second tube delimiting a containment space around the first tube, this space communicating with the pumping means, a means associated with the first tube for increasing the liquid/vapour contact time in the containment space, means for homogenizing the boiling temperature and at least one thermostat-controlled enclosure.

According to an embodiment, the device comprises two identical ebulliometers into which two liquids are respectively fed, one being a pure solvent and the other a solution of a solute in this solvent, a means for measuring the difference between the temperatures prevailing respectively in the containment spaces delimited by the second tubes of the two ebulliometers, and a means for determining the molar mass of the solute from the measured temperature difference.

According to another embodiment, the means for homogenizing the boiling temperature in each ebulliometer include circuits for delivering gas into the liquid.

According to another embodiment, each ebulliometer comprises a pointed element intended to prevent formation of liquid droplets in the vicinity of the measuring means.

According to another embodiment, the means for condensing the vapour in each ebulliometer comprise a circuit external to the vessel, suited to recycle the condensed liquid by thermosiphoning, this circuit communicating by means of a refrigerating column with a pressure and discharge system.

According to another embodiment, the pressure and discharge system comprises for example a moisture absorption column.

The means for boiling each liquid substance comprise for example a heat plug in each ebulliometer, these plugs being connected to a common power supply.

According to an embodiment, the first thermostat-controlled enclosure is a solvent vapour oven provided with an external circuit for vapour condensation and recycling by thermosiphoning, which communicates with a refrigerating column and with said pressure and discharge system, the device also comprising a second enclosure including the first enclosure with its external circuit, and heating and temperature control means in this second enclosure.

The stability obtained by the device is of the order of one ten thousandth of a degree (0.0001), which allows to precisely determine molar masses of solute around 10,000 g/mol with solute concentrations below 1 g/1000 g solvent.

As shown in the description hereafter, various factors contribute to the stability of the temperature obtained in each ebulliometer and in the two ebulliometers with a comparative assembly.

BRIEF DESCRIPTION OF THE DRAWINGS

Other features of the device according to the invention will be clear from reading the description hereafter of a non limitative example, with reference to the accompanying drawings wherein.

DETAILED DESCRIPTION

Figure 1:
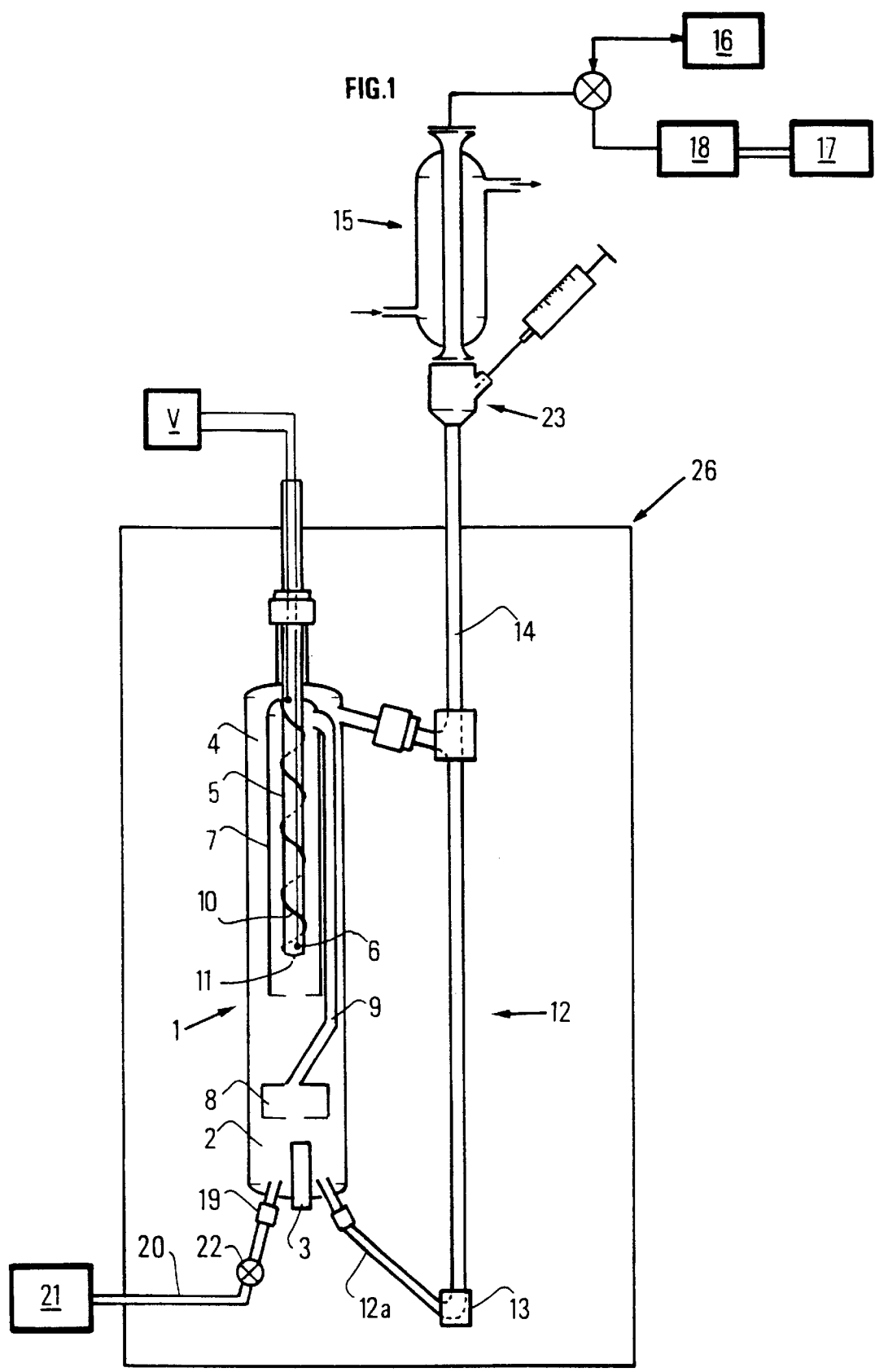
FIG. 1 diagrammatically shows a preferred ebulliometer mode.

The ebulliometer of FIG. 1 comprises an elongate vessel 1 made of stainless steel for example, arranged vertically, into which the substance to be measured is fed. The lower part 2 is a boiler of about 5 to 30 ml capacity, where the substance is boiled by a heating means such as a plug 3. The upper part 4 is a vapour chamber. A tube or glove finger 5 through which a thermocouple 6 connected to a temperature measuring means V is lowered opens into the upper part of the vessel through a neck. Vapour chamber 4 contains, around finger 5, a containment tube or basket 7 closed at its upper end for channelling the stream injected. A pump 8, for example a Cottrel type pump, is placed in boiler 2. Through a tube 9, pump 8 sprays into basket 7 a mixture of vapour and of liquid droplets. A coil 10 is arranged around finger 5 in order to increase the liquid-vapour contact time in the measuring zone around thermocouple 6 and thereby to ensure better temperature equilibrium. At the lower end of finger 5, coil 10 is preferably ended by a metal point 11 which prevents formation of drops in the vicinity of the measuring zone, thus providing better stability without local overheating.

The ebulliometer comprises a vapour recycling circuit 12 connected, on the one hand, to vapour chamber 4 outside the basket and, on the other hand, to boiler 2 by an inclined bend 12 provided with a drain valve 13 with a low dead volume. Recycling circuit 12 is connected by a tube 14 to a water-circulation refrigerating column 15 and it communicates with either pressure means 16 intended to establish a reference pressure or, at the end of the measurement, to a vacuum chamber 17 by means of a drying column 18 containing a substance that absorbs the moisture inside the ebulliometer, such as a dibutylphthalate solution. The vapour discharged from chamber 4 after a residence time passes into refrigerating column 15. It condenses and meets the liquid set into motion by natural thermosiphoning due to the particular geometry of recycling bend 12a.

A connector 19 at the base of boiler 2 allows connection of a tube 20 connected to a nitrogen tank 21 intended to control the temperature of boiler 2. A needle valve 22 allows fine adjustment of the flow of nitrogen, which guarantees good bubble nucleation and therefore good ebullition control. Part of the possible overheating is thus carried off in the nitrogen stream.

A special connector 23 arranged at the top of the refrigerating column allows connection of either a syringe or a HPLC type pump to feed the substance into the ebulliometer. The latter is arranged in a thermostat-controlled enclosure.

The temperature measuring precision allowed by each of these ebulliometers hangs on various factors:

vapour recycling generates no heat exchange with the outside, thermosiphoning circuit 12 being inside the enclosure, the contact time (or path) between the liquid phase and the vapour phase in the vicinity of the measuring point is increased by the presence of coil 10 around the finger protecting the thermocouple, metal point 11 at the base of the measuring zone prevents the formation of liquid droplets and thus limits local overheating risks, containment tube or basket 7 around finger 5 protecting the temperature detector channels the stream in a limited zone by limiting random liquid ejections, injection of gas at the base of the vessel, controlled very precisely (by means of a needle valve for example), allows good ebullition control.

A weld of thermocouple 6, referred to as measuring weld, is placed at the liquid/vapour equilibrium point in the vicinity of point 11; the other weld, referred to as reference weld, is placed above, at a level that can only be reached by the vapour.

Comparative assembly

Figure 2:
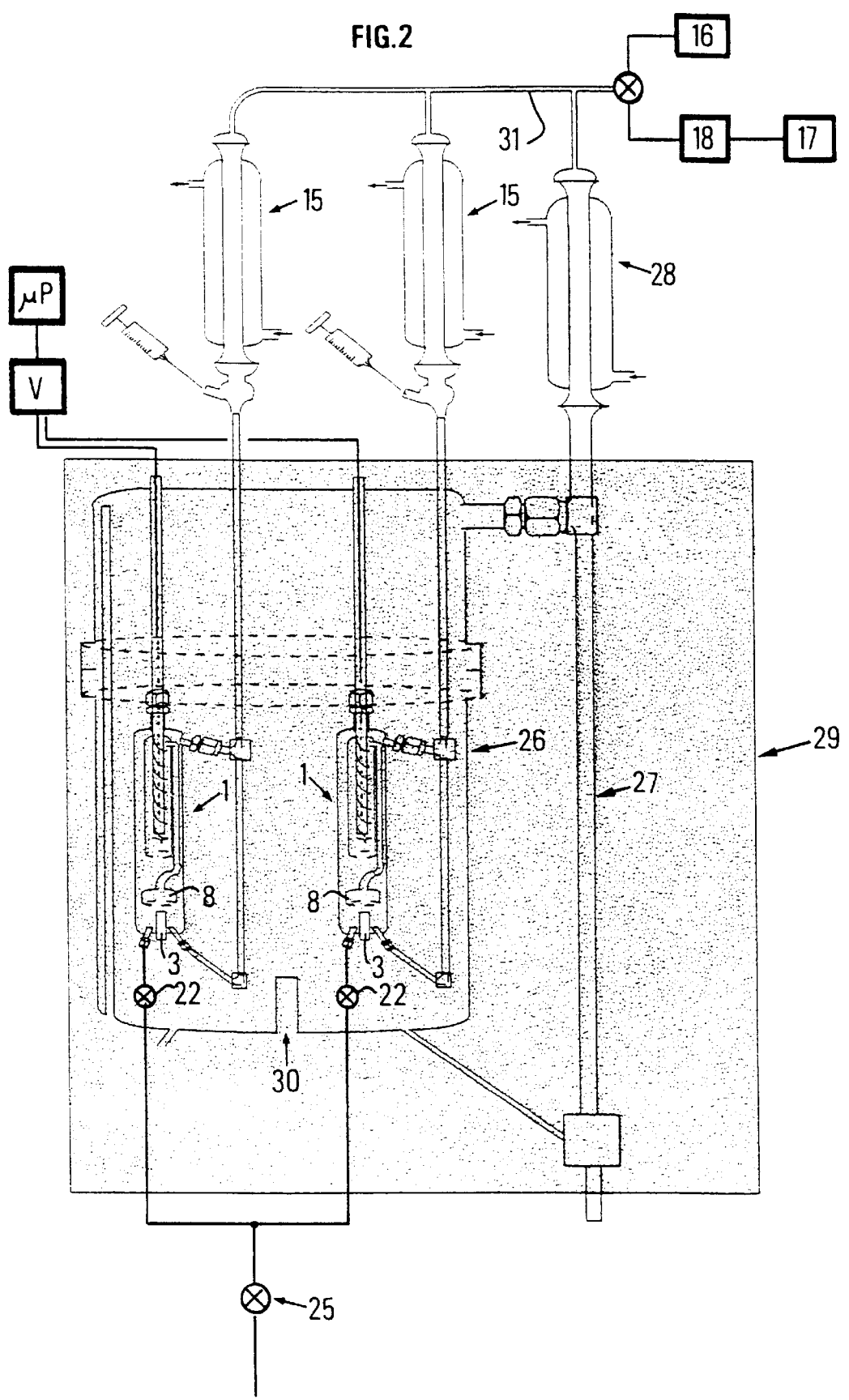
FIG. 2 diagrammatically shows a comparative assembly with two ebulliometers of the type shown in FIG. 1, installed in temperature-controlled enclosures.

The ebulliometer described above can be used alone. However, the temperature measurements provided thereby are subject to possible variations because, if the sample studied contains volatile products, part thereof changes to the vapour phase and the boiling point of the solution is modified. In order to overcome this fluctuation problem, the comparative assembly shown in FIG. 2 is preferably used, with two identical ebulliometers 1 placed in the same thermostat-controlled enclosure 26.

A solution consisting of a solvent and of a solute is fed into the first ebulliometer; pure solvent is fed into the second one and a single thermocouple is used, whose welds are placed respectively in the two baskets at the respective liquid/vapour equilibrium points.

Heat plugs 3 of the two ebulliometers are preferably connected in parallel to a stabilized power supply (not shown) so as to have only one heating circuit for the two plugs and therefore to avoid a possible source of dispersion.

The thermocouple is connected to a voltmeter V precise to $10^{-7}$ volts, giving an emf converted into a temperature difference $\Delta T$ by means of the calibration polynomial. Needle valves 22 allow fine adjustment of the flow of nitrogen in each boiler and an "on-off" type valve 25 placed upstream from the others provides rougher adjustment.

Thermal insulation of the ebulliometers is provided by two stainless steel housings forming a Faraday shield, which allows to limit electric interferences. The first housing 26 is a solvent vapour circulation oven whose lower and upper parts are externally interconnected by a circuit 27 communicating with a refrigerating column 28. The oven is maintained at a strictly constant temperature by a temperature control means (not shown) actuating a heat plug 29. The second housing 30, which contains the first one, is filled with a heat-insulating material such as glass wool.

The two ebulliometers 1 are connected to a common circuit 31 above refrigerating columns 15, this circuit communicating with a common system comprising pressure means 16 intended to establish a reference pressure and, at the end of the measuring procedure, to a primary vacuum pump 17 protected by means of a liquid nitrogen trap, by means of a drying column 18 using a dibutylphthalate solution. Pump 17 allows vacuum drying of the whole common system and the drying column filled with silica gel provides effective protection against any atmospheric pollution through moisture, water being slightly soluble in the solvents, which is a factor of error for measurements.

A microprocessor $\mu$P connected to measuring means V can directly deduce the molar mass of the solute, in a way known in the art, from this differential temperature measurement between the temperature at equilibrium of the pure solvent and of the solution of a certain solute dissolved in the solvent respectively.

What is claimed is:

1. An ebulliometric device for measuring with high precision a physical parameter of liquid substances, comprising at least one ebulliometer including an elongate vessel into which a liquid substance is fed, means for boiling the liquid, a means for measuring the boiling-point temperature arranged in the upper part of the vessel, a pumping means allowing to spray substance in the form of liquid and vapour in the upper part of the vessel, means external to the vessel for condensation of the vapour allowing to recycle it to the base of the vessel, characterized in that it comprises a first tube in which temperature measuring means is located in the upper part of the vessel, a second tube delimiting a containment space around said first tube, this space communicating with said pumping means, a means associated with said first tube for increasing the liquid/vapour contact time in the containment space, means for homogenizing the boiling temperature and at least one thermostat-controlled enclosure, a device characterized in that it comprises two identical ebulliometers into which two liquids are respectively fed, one being a solvent, the other a solution of a solute in this solvent, a means (V) for measuring the difference between the temperatures respectively prevailing in the containment spaces delimited by second tubes of the two ebulliometers, and a means ($\mu$P) for determining the molar mass of the solute from the measured temperature difference characterized in that said means for condensing the vapour in each ebulliometer comprise a circuit external to vessel, suited to recycle the condensed liquid by thermosiphoning, this circuit communicating by means of a refrigerating column with a pressure and discharge system.

2. A device as claimed in claim 1, characterized in that the pressure and discharge system comprises a moisture absorption column.

3. A device as claimed in claim 1, characterized in that said means for boiling each liquid substance comprise a heat plug in each ebulliometer, these plugs being connected to a common power supply.

4. A device as claimed in claim 1 characterized in that said first thermostat-controlled enclosure is a solvent vapour oven provided with an external circuit for vapour condensation and recycling by thermosiphoning, which communicates with a refrigerating column, and with said pressure and discharge system, the device comprising a second enclosure including the first enclosure with its external circuit, and said heating and temperature control means in this second enclosure.

5. A device as claimed in claim 1, characterized in that said pressure and discharge system comprises a drying column.

6. An ebulliometric device for measuring with high precision a physical parameter of liquid substances, comprising an ebulliometer including an elongate vessel into which a liquid substance is fed, means for boiling the liquid, a sensor for measuring the boiling-point temperature arranged in the upper part of the vessel, a pump allowing to spray substance in the form of liquid and vapor in the upper part of the vessel, an assembly external to the vessel for condensing the vapor allowing to recycle the condensed vapor to the base of the vessel and at least one thermostat-controlled enclosure, the device also comprising a first finger tube extending in the elongate vessel from an upper part of the same for protecting the sensor, an element in close contact with the first finger tube for increasing a time of contact of liquid and vapor with the finger tube, a second tube delimiting a containment space around the first tube and the element, this space communicating with the pump through a duct, and a gas injecting means at an lower part of the elongate vessel for controlling the boiling temperature.

7. A device as claimed in claim 6, also comprising a pointed element for preventing formation of liquid droplets in the vicinity of the sensor.

8. A device a claimed in claim 7, wherein the assembly for condensing the vapor in the ebulliometer comprises a circuit external to the vessel, for recycling the condensed liquid by theromosiphoning, the circuit communicating with a pressure and discharge system through a refrigerating column.

9. A device as claimed in claim 7, wherein the assembly for condensing the vapor in the ebulliometer comprises a circuit external to the vessel, for recycling the condensed liquid by thermosiphoning, the circuit communicating through a refrigerating column with a pressure and discharge system including a moisture absorption column.

10. A device as claimed in claim 7, wherein the means for boiling each liquid comprise a heat plug connected with a power supply.

11. A device a claimed in claim 7, wherein said first thermostat-controlled enclosure is a solvent vapor oven provided with an external circuit for vapor condensation and recycling by thermosiphoning, which communicates with a refrigerating column, and with said pressure and discharge system, the device comprising a second enclosure including first enclosure with its external circuit, and said heating and temperature control means in this second enclosure.

12. A device as claimed in claim 7, wherein said pressure and discharge system comprises a drying column.

13. An ebulliometric device for measuring with high precision a physical parameter of liquid, comprising at least two ebulliometers including each an elongate vessel into which a liquid is fed, the liquid substance in the first ebulliometer being a solvent and the liquid substance in the second ebulliometer being a solution of a solute in the solvent, means for boiling the liquid, a sensor for measuring the boiling-point temperature arranged in the upper part of the vessel, a pump allowing to spray substance in the form of liquid and vapor in the upper part of the vessel, an assembly external to the vessel for condensing the vapor allowing to recycle the condensed vapor to the base of the vessel and at least one thermostat-controlled enclosure, a first finger tube extending in the elongate vessel from an upper part of the same for protecting the sensor, an element in close contact with the first finger tube for increasing a time of contact of the liquid and vapor with the finger tube, a second tube delimiting a containment space around first tube and the element, this space communicating with the pump through a duct, a gas injecting means at an lower part of the elongate vessel for controlling the boiling temperature, means for measuring a difference between temperatures respectively prevailing in said respective containment spaces, and a calculator ($\mu$P) for determining a molar mass of the solute from the measured temperature difference.

14. A device as claimed in claim 13, wherein each ebulliometer also comprising a pointed element for preventing formation of liquid droplets in the vicinity of the sensor.

15. A device as claimed in claim 14, wherein the assembly for condensing the vapor in each ebulliometer comprises a circuit external to the vessel, for recycling the condensed liquid by thermoisphoning, the circuit communicating with a pressure and discharge system through a refrigerating column.

16. A device as claimed in claim 14, wherein the assembly for condensing the vapor in each ebulliometer comprises a circuit external to the vessel, for recycling the condensed liquid by thermosiphoning, the circuit communicating through a refrigerating column with a pressure and discharge system including a moisture absorption column.

17. A device as claimed in claim 14, wherein the means for boiling each liquid substance comprises a heat plug in each ebulliometer, the heat plugs being connected to a common power supply.

18. A device as claimed in claim 14, wherein said first thermostat-controlled enclosure is a solvent vapor oven provided with an external circuit for vapor condensation and recycling by thermosiphoning, which communicates with a refrigerating column, and with said pressure and discharge system, the device comprising a second enclosure including a first enclosure with its external circuit, and said heating and temperature control means in this second enclosure.

19. A device as claimed in claim 14, wherein in that said pressure and discharge system comprises a drying column.

* * * * *